(12) United States Patent  (10) Patent No.: US 8,423,385 B2
Radoccia et al.  (45) Date of Patent: Apr. 16, 2013

(54) ELECTRONIC PATIENT REGISTRATION VERIFICATION AND PAYMENT SYSTEM AND METHOD

(75) Inventors: Richard A. Radoccia, Laurel, NY (US); Rob G. Hampton, Green Bay, WI (US)

(73) Assignee: ClipboardMD, Inc., Laurel, NY (US)

( * ) Notice: Subject to any disclaimer, the term of this patent is extended or adjusted under 35 U.S.C. 154(b) by 215 days.

(21) Appl. No.: 12/386,144

(22) Filed: Apr. 14, 2009

(65) Prior Publication Data

US 2009/0271220 A1    Oct. 29, 2009

Related U.S. Application Data

(60) Provisional application No. 61/124,083, filed on Apr. 14, 2008, provisional application No. 61/189,437, filed on Aug. 19, 2008.

(51) Int. Cl.
*G06Q 10/00*    (2006.01)

(52) U.S. Cl.
USPC .................................................. 705/3; 705/2

(58) Field of Classification Search ................... 705/2, 3
See application file for complete search history.

(56) References Cited

U.S. PATENT DOCUMENTS

| | | | |
|---|---|---|---|
| 2003/0018496 A1* | 1/2003 | Hambright et al. | 705/2 |
| 2004/0117617 A1 | 6/2004 | Geller et al. | 713/156 |
| 2007/0288254 A1* | 12/2007 | Eisner | 705/1 |
| 2008/0033750 A1* | 2/2008 | Burriss et al. | 705/2 |

OTHER PUBLICATIONS

Certain selected pages from website www.medfusion.net downloaded and printed on Aug. 11, 2009.
Certain selected pages from website www.phreesia.com downloaded and printed on Aug. 11, 2009.
Certain selected pages from website www.nomoreclipboard.com downloaded and printed on Aug. 11, 2009.

* cited by examiner

*Primary Examiner* — Robert Morgan
*Assistant Examiner* — Maroun Kanaan
(74) *Attorney, Agent, or Firm* — Gerald T. Bodner

(57) ABSTRACT

A patient registration record and payment system creates, maintains and transfers all relevant data electronically. The system captures patient registration and payment data, such as personal, demographic and insurance coverage information, medical history, frequently accessed healthcare providers, and data specifying one or more funding sources to pay for the amount of a medical visit for which the patient is responsible at the time of entry using graphical user interfaces through the Internet or a local area network. Moreover, the system includes the capability to access reference databases regarding verification of data for accuracy, completeness and validity on a continuous, automated basis and, where such reference databases are not available, to initiate manual verification of data for accuracy, completeness and validity by system personnel prior to making patient registration data available to customers or transferring such data to customer databases. Additionally, the system provides for an automated process to transfer payment from one or more funding sources specified by the patient at the time of entry to a deposit account specified by the healthcare provider.

31 Claims, 5 Drawing Sheets

Electronic Patient Registration Verification and Payment System

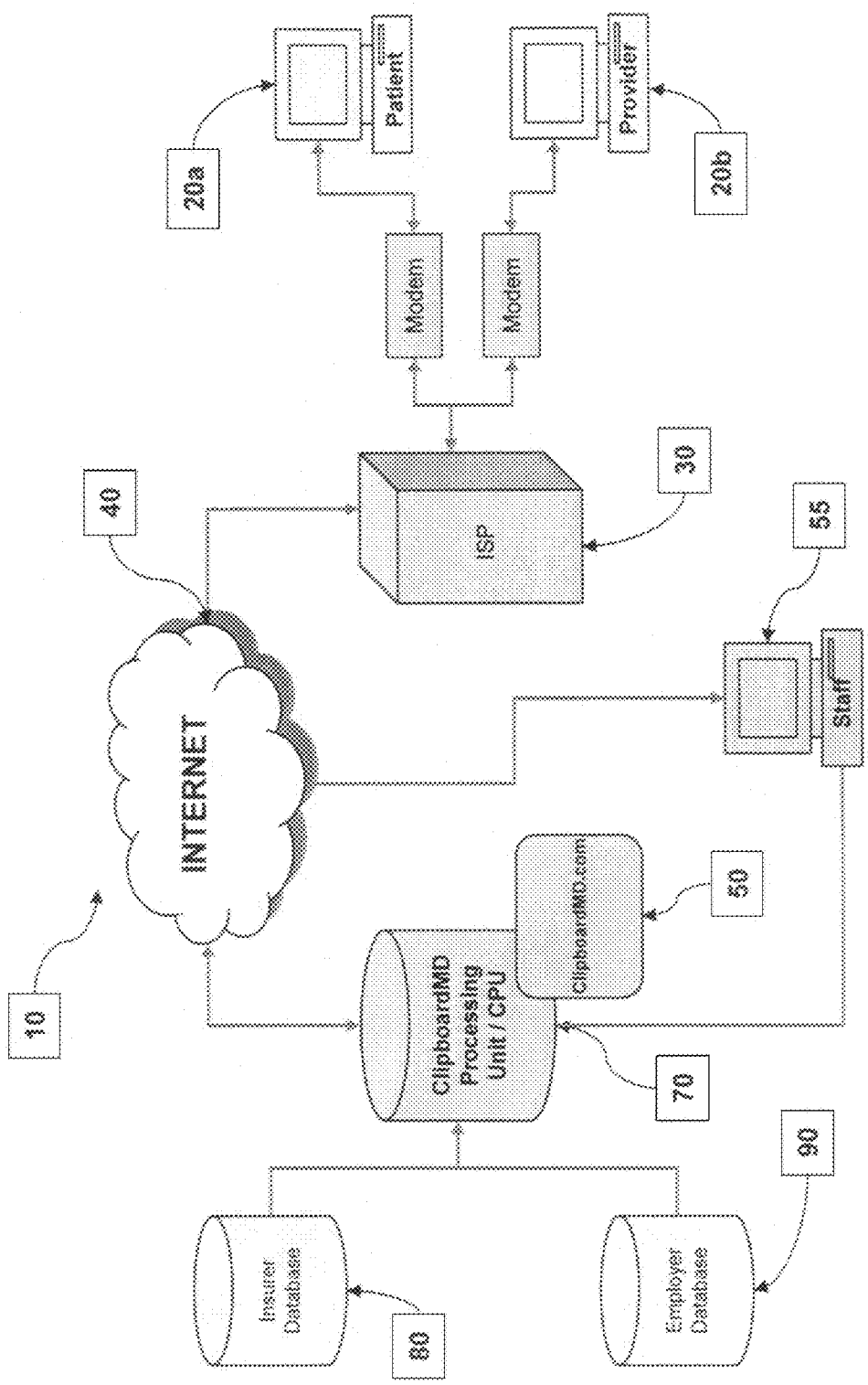
Figure 1 – Electronic Patient Registration Verification and Payment System

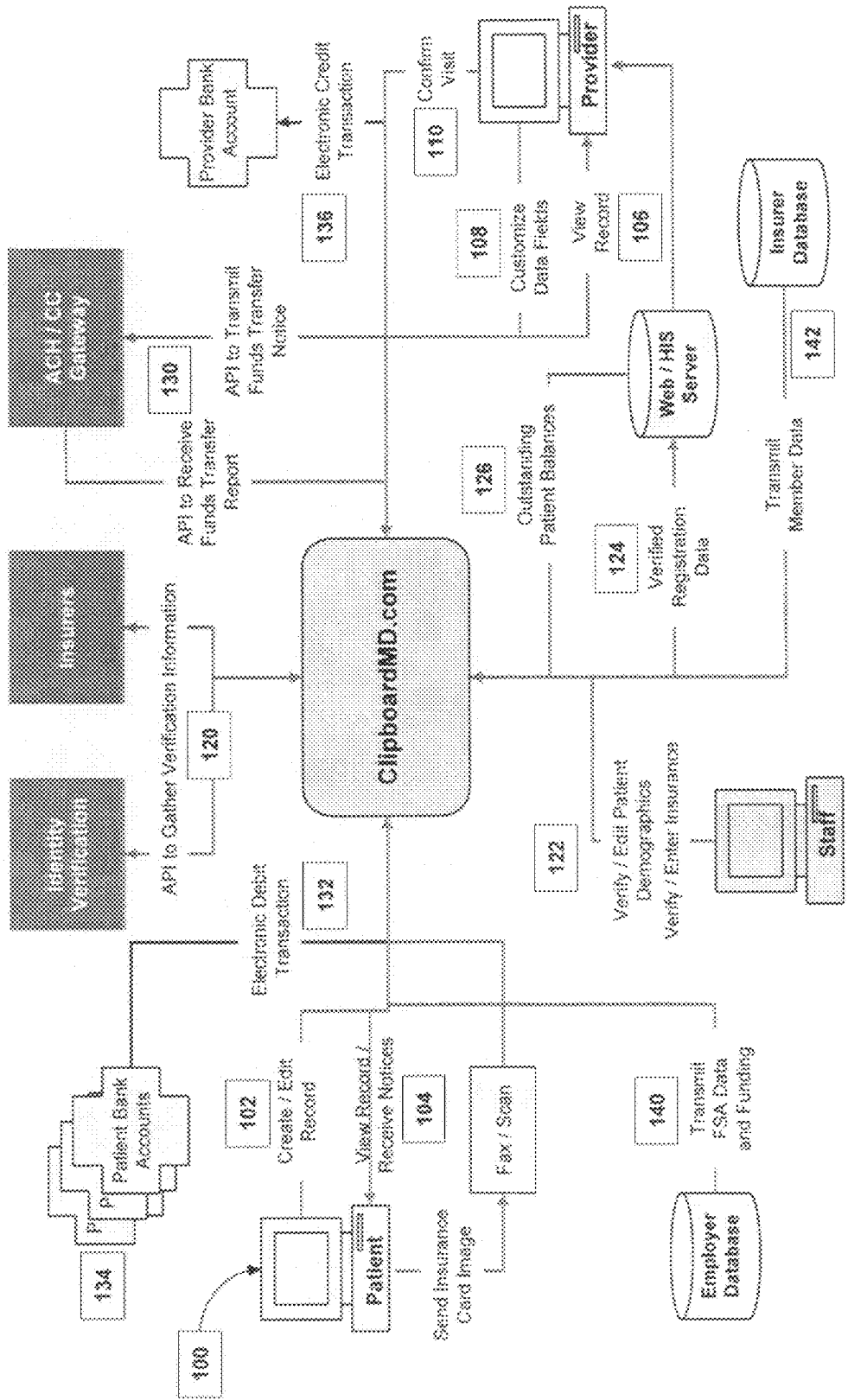
Figure 2 – Graphical Illustration of Invention Relationships

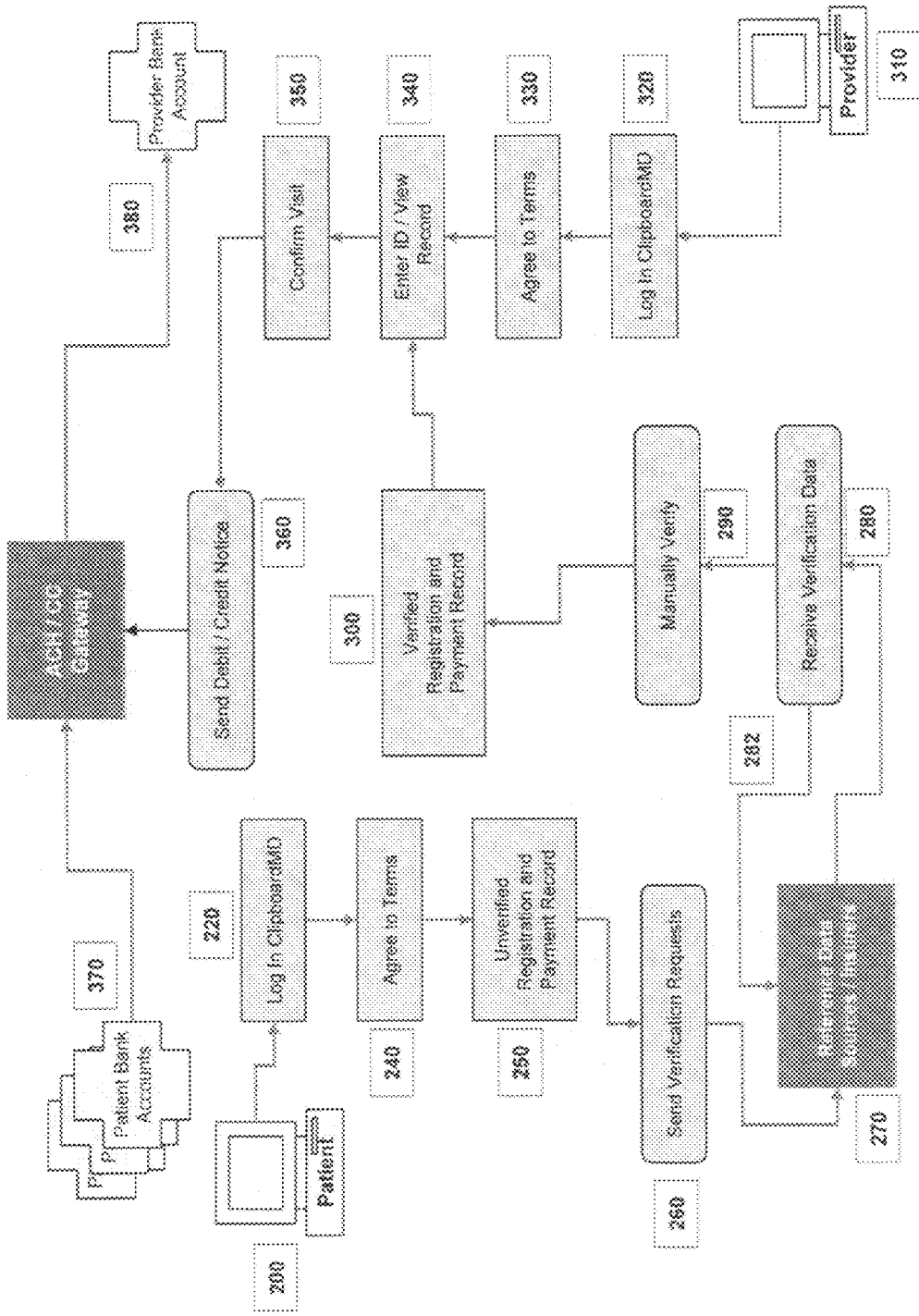
Figure 3 – Flow Chart of Patient Registration Verification and Payment Process

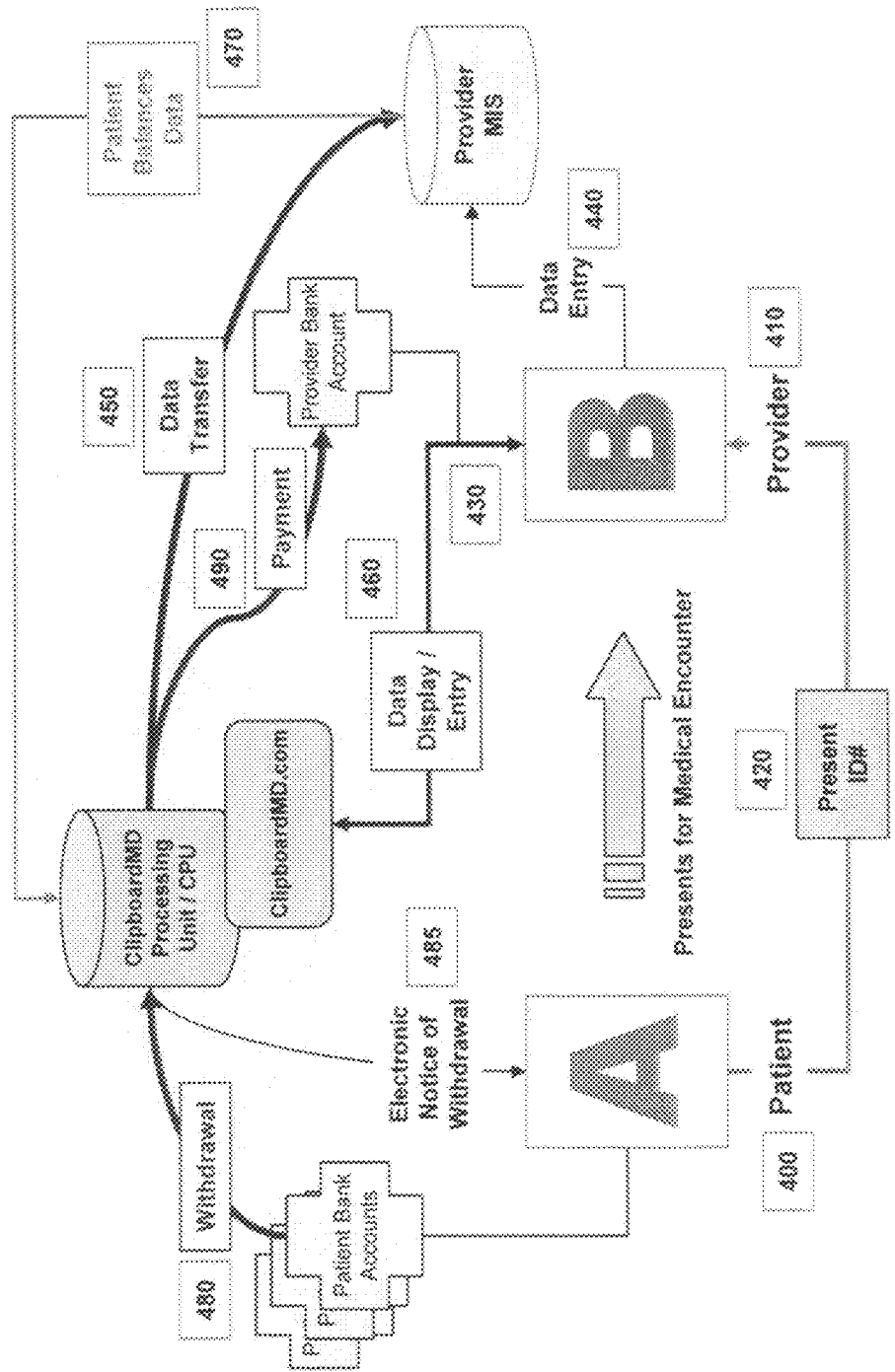
Figure 4 – Exemplary Patient – Provider Encounter Process

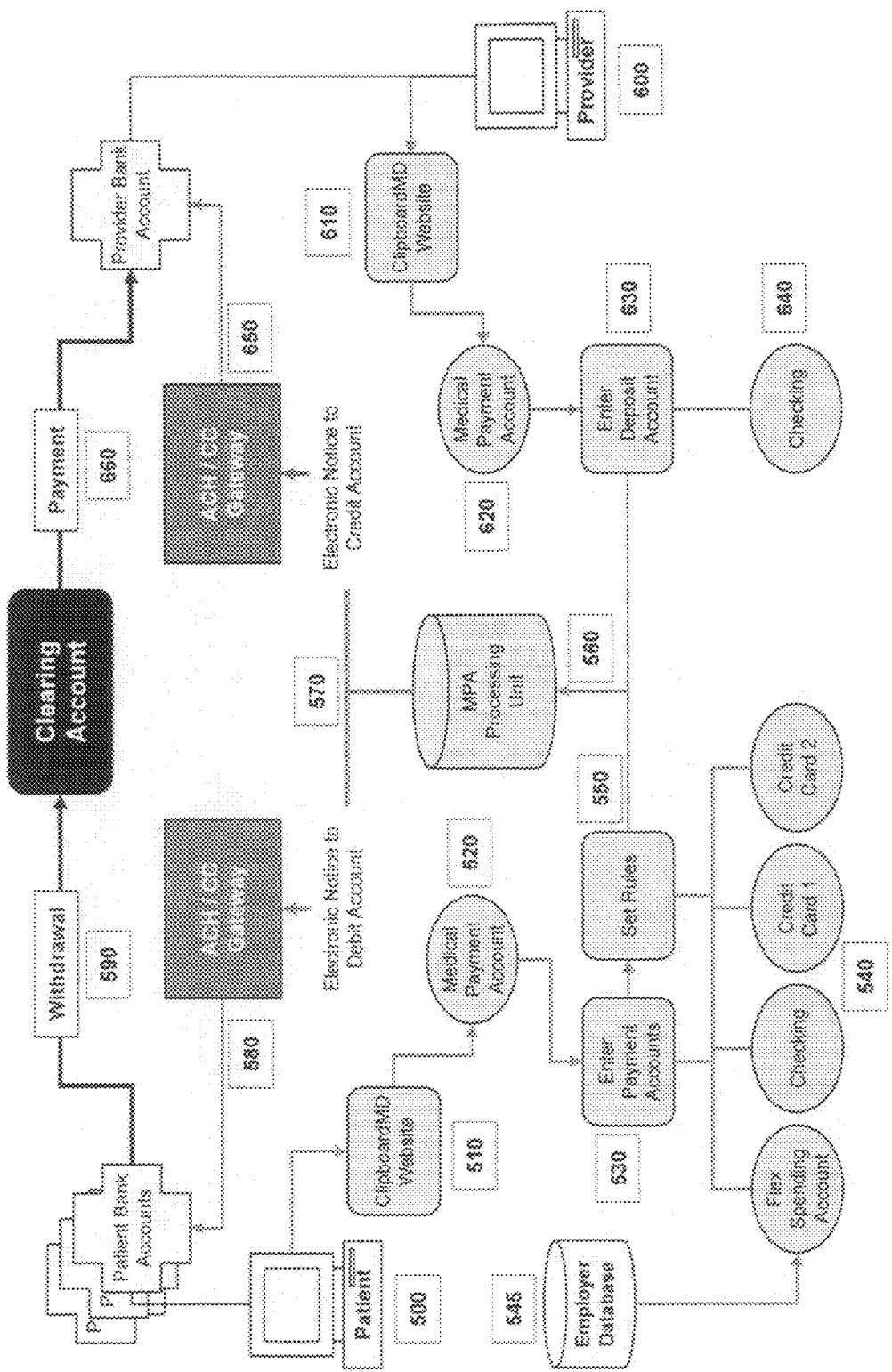

ELECTRONIC PATIENT REGISTRATION VERIFICATION AND PAYMENT SYSTEM AND METHOD

CROSS REFERENCE TO RELATED APPLICATIONS

This application is related to U.S. Provisional Application Ser. No. 61/124,083, filed on Apr. 14, 2008, and entitled "Web Based Healthcare Information System", and U.S. Provisional Application Ser. No. 61/189,437, filed on Aug. 19, 2008, and entitled "Web Based Healthcare Information System and Method", the disclosures of which are incorporated herein by reference and on which priority is hereby claimed.

BACKGROUND OF THE INVENTION

1. Field of the Invention

The present invention generally relates to electronic data management systems, and more particularly relates to a system for storing, continually verifying, retrieving and transferring patient registration and payment records and funds in a global network environment.

2. Description of the Prior Art

Patients are required to transfer information about their identity, insurance coverage and medical history prior to being treated by a healthcare practitioner, such as a physician, or prior to being admitted to a hospital. This is usually performed by having the patient manually enter such information on a set of paper forms. The same patient must repeat this process prior to treatment by each new healthcare provider for the first time and for the same healthcare provider no less than once per year, as required by federal and state regulations.

For the healthcare provider obtaining this information, the information inscribed by the patient on paper forms must be manually entered into an electronic data processing system by their administrative or clerical personnel. Additionally, the personnel must undertake a range of tasks to verify the information given by the patient in order to properly bill the patient's insurer for the service rendered to the patient. Overall, the complete process is labor-intensive and therefore costly. Estimates offered by recognized industry experts indicate the total costs of the process range from $6 to $12 per patient encounter or visit.

When the information given by the patient is incomplete or invalid, or when errors occur during the manual entry of the information by the administrative or clerical staff of the healthcare provider into the electronic data processing system, the likelihood that the healthcare provider will receive proper payment from the patient's insurer declines. In recent years, federal regulations have encouraged or required healthcare providers to utilize electronic methods to transmit medical services bills to a patient's insurer. Electronic methods are binary (digital) so that the format and value of each data point transmitted by the healthcare provider must match precisely to the format and value of the data point that resides on the electronic data processing system of the insurer in order to be accepted. The mismatch of a single data point may be sufficient for a medical services bill transmitted electronically by a healthcare provider to be rejected by the insurer, thereby denying the healthcare provider of payment for the medical services rendered to the patient. Additionally, insurers have imposed limits on the amount of time a healthcare provider has to transmit a medical services bill. If a patient record is either lacking or incorrect, a healthcare provider must complete or correct the record within the set timeframe in order to be eligible for payment.

As specified by the terms of their health insurance policy, patients may be required to make a payment prior to receiving treatment by a healthcare provider. This payment is typically classified as the patient co-payment. In the past, a healthcare provider may have agreed to mail a bill to the patient at a later date for the amount of the co-payment. However, in recent years, typical health insurance policies have increased the magnitude of the co-payment. As the patient co-payment has become more substantial, healthcare providers have increasingly required the patient to make the payment prior to receiving treatment in lieu of mailing a bill at a later date. And since not all healthcare providers accept the same form of payment, a patient may not receive treatment because the patient did not possess the specific form of payment required by the healthcare provider.

It may be possible for the healthcare provider to create a system that captures patient registration at the time of entry using graphical user interfaces through a network. However, because these systems are limited by the network and exclusively for use by a specific healthcare provider, the patient is not able to use that system with, and must therefore repeat the process for, other unrelated healthcare providers. Such systems also do not include the capability to access reference databases regarding verification of data for accuracy, completeness and validity on a continuous, automated basis and, where such reference databases are not available, to initiate manual verification of data for accuracy, completeness and validity by system personnel.

In addition, it may be possible for patients to use other systems that capture patient registration at the time of entry using graphical user interfaces through a global network environment. However, these systems simply pass on information entered by patients and do not employ automated procedures to continually verify and retrieve data from reference databases or initiate manual verification by system personnel prior to making such data available to customers or transferring such data to customer databases. Without such an interim procedure, the likelihood that the healthcare provider will receive proper payment from the patient's insurer is not improved.

Further, other systems that capture patient registration at the time of entry using graphical user interfaces through a global network environment do not include the capability for patients to specify one or more funding sources to pay for the amount of a medical visit for which the patient is responsible, nor do such systems include an automated process to transfer payment from the one or more funding sources specified by the patient at time of entry to a deposit account specified by the healthcare provider.

OBJECTS AND SUMMARY OF THE INVENTION

It is an object of the present invention to provide an electronic patient registration verification and payment system and method which create, maintain and transfer all relevant data electronically.

It is another object of the present invention to provide an electronic patient registration verification and payment system which has the capability to access reference databases regarding verification of a patient's registration data for accuracy, completeness and validity on a continuous, automated basis.

It is still another object of the present invention to provide an electronic patient registration verification and payment system which can initiate manual verification of registration data for accuracy, completeness and validity by system personnel when patient reference databases are not available and prior to making patient registration data available to customers, such as healthcare providers, or transferring such data to customer databases.

It is yet another object of the present invention to provide an electronic patient registration verification and payment system which automatically transfers payment from one or more funding sources specified by the patient at the time of entry to a deposit account specified by a healthcare provider.

It is yet a further object of the present invention to provide an electronic patient registration verification and payment system which minimizes or eliminates the chance that a patient may be refused treatment because the patient did not possess the specific form of payment required by the healthcare provider.

It is still another object of the present invention to provide an electronic patient registration verification and payment system which ensures that the healthcare provider will receive proper payment from the patient's insurer.

It is yet a further object of the present invention to provide an electronic patient registration verification and payment system which overcomes the inherent disadvantages of conventional patient registration systems.

In one aspect of the present invention, a method for electronically verifying and transferring information includes the steps of collecting received registration and payment information from patients in a common format through an interface to a global network, storing collected registration and payment information in a dynamic database, and verifying collected registration and payment information with external sources through electronic interfaces prior to electronically transferring such information to the healthcare provider.

In another aspect of the present invention, a system for electronically verifying and transferring information includes means for collecting received registration and payment information from patients in a common format through an interface to a global network, means for storing collected registration and payment information in a dynamic database, and means for verifying collected registration and payment information with external sources through electronic interfaces prior to electronically transferring such information to the healthcare provider.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 1 is a simplified block diagram of an electronic patient registration verification and payment system formed in accordance with an exemplary embodiment of the present invention.

FIG. 2 is a graphical illustration of the relationships of the patient, healthcare provider, employer, insurer, electronic verification sources and verification specialists, and an electronic patient registration verification and payment system formed in accordance with an exemplary embodiment of the present invention.

FIG. 3 is a graphical illustration of the logic flow of an electronic patient registration verification and payment process in accordance with an exemplary embodiment of the present invention.

FIG. 4 is a flow chart illustrating the process of a patient-healthcare provider encounter using an electronic patient registration verification and payment system formed in accordance with an exemplary embodiment of the present invention.

FIG. 5 is a graphical illustration of the logic flow of an online payment transfer process in accordance with an exemplary embodiment of the present invention.

DETAILED DESCRIPTION OF THE PREFERRED EMBODIMENTS

An exemplary embodiment of a web-based patient registration and payment information acquisition, storage, verification, retrieval and transfer system (also referred to herein by the trademark/service mark ClipboardMD) formed in accordance with the present invention automates and simplifies existing methods of patient registration and payment information collection, verification, audit, maintenance, retrieval and transfer. In one form of the present invention, the system captures payment information, but does not pass that information on to the healthcare provider. All the healthcare provider knows is that it received payment from the system and will not know how the patient paid the system the funds the system used to pay the healthcare provider. In contrast to other conventional systems, the described exemplary embodiment of the present invention creates and maintains all patient registration and payment information electronically and thus can eliminate or supplement the creation and maintenance of physical data records and the associated manual steps associated with processing them. An exemplary ClipboardMD system may further provide an intuitive, easy-to-use, web-based interface that allows users to capture, display and transfer verified patient registration information and payment quickly and efficiently. In accordance with an exemplary embodiment of the present invention, patient registration and payment information may also be directly entered online by a patient into the ClipboardMD system. Alternatively, patient registration and payment information may be entered into the electronic registration verification and payment system from paper-based forms, or may be imported from electronic storage devices (CDROM, data file or the like) from the patient's employer or insurer.

The described exemplary ClipboardMD system of the present invention enables the healthcare provider to capture verified patient registration information and receive patient payment with a single ClipboardMD identification number. In one embodiment, the healthcare provider logs into the exemplary online registration and payment system and enters the patient identification number. In accordance with an exemplary embodiment, the verified registration information for the patient is displayed for viewing or printing by the healthcare provider. Alternatively, the verified registration information is electronically transferred directly to the web-servers of the healthcare provider's online information technology system through, for example, a secure electronic interface. An exemplary ClipboardMD system may, upon the online entry by or electronic import of data from the healthcare provider confirming the visit by the patient, further initiate a series of electronic instructions to a financial automated clearinghouse to transfer funds from one or more of the previously specified financial accounts of the patient to a previously specified financial account of the healthcare provider.

In addition, the described exemplary ClipboardMD system of the present invention may include the capability to manage and report on a wide variety of information formats, including patient registration and payment information from external sources, such as insurers, employers, government and reference databases, and financial institutions. In accordance with an exemplary embodiment, the ClipboardMD system may continuously access such external sources to validate and verify current patient registration and payment information prior to transferring at least the patient registration information to the healthcare provider. The ClipboardMD system may then alert the healthcare provider of any information not validated or verified by an external source as well as to information reported by the source but not recorded in the patient record.

The described exemplary ClipboardMD system of the present invention may also prompt patients to renew registration and payment information prior to the expiration of that information. Such prompts may be communicated to the patient, for example, by email or text notification to the address previously specified by the patient.

FIG. 1 illustrates an exemplary electronic patient registration and payment system 10 formed in accordance with the present invention. The described exemplary electronic patient registration and payment system 10 includes multiple remote devices 20a and 20b, such as personal computers (PCs) and the like, coupled to one or more web servers 30, such as an Internet service provider (ISP), through a remote communication network 40, such as the Internet or Ethernet. The communication network may refer to a network or combination of networks spanning any geographical area, such as a local area network, wide area network, regional network, national network, and/or global network. The Internet is an example of a current global computer network. In addition, the communication network 40 may be a hardwire network, wireless network, or a combination of hardwire and wireless networks.

Hardwire networks may include, for example, fiber optic lines, cable lines, integrated digital services network (ISDN) lines, copper lines, etc. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

The remote devices 20a-20b may be general purpose computing devices that allow users (e.g., patients, healthcare providers, and others) to remotely communicate with the web server over the communication network 40. The computing devices may be any processor controlled device that permits access to the communication network, including terminal devices, such as personal computers, workstations, servers, clients, mini-computers, mainframe computers, laptop computers, a network of individual computers, mobile computers, palm-top computers, handheld computers, set top boxes for a television, other types of web enabled televisions, interactive kiosks, personal digital assistants, interactive or web enabled wireless communications devices, mobile web browsers, or a combination thereof.

The computers may comprise one or more input devices such as a keyboard, mouse, touch pad, joystick, pen input pad, and the like. The computers may also possess an output device, such as a visual display and an audio output. One or more of these computing devices may form a computing environment.

A processing unit 70 (also referred to herein as the ClipboardMD processing unit) preferably hosts a website 50 comprising one or more interrelated web page files and other files and programs. The files and programs may be accessed via a communications network 40 such as the Internet, by sending for example, a hypertext transfer protocol (HTTP) request specifying a uniform resource locator (URL) that identifies the location of one of said web page files, wherein the files and programs are owned, managed or authorized by a single entity. Such files and programs can include, for example, hypertext markup language (HTML) files generated from Microsoft.NET platform integrated with Macromedia Flex. The described ClipboardMD processing unit 70 may also import information from a variety of external data sources such as, for example, the data storage servers and databases of employers and health insurers 80, 90.

The ClipboardMD processing unit 70 may include a microprocessor and software which carry out the operations and functions of the system. The ClipboardMD processing unit 70 is preferably operatively coupled to a personal computer 75 or like device for operation by ClipboardMD personnel and verification specialists.

In an exemplary embodiment, the web page files preferably include a home page file that corresponds to a home page of the website. The home page can serve as a gateway or access point to the remaining files and programs contained within the website. In one embodiment, all of the files and programs may be located under, and accessible within, the same network domain as the home page file. Alternatively, the files and programs can be located and accessible through several different network domains.

The described exemplary website may use encryption technology such as for example secure socket layer (SSL) encryption and digital certificates to maintain the integrity and confidentiality of electronic transmissions to and from the ClipboardMD processing unit 70. In the described exemplary embodiment message data is encrypted using a randomly generated key that is further encrypted using the recipient's public key. This is referred to as the "digital envelope" of the message which is sent to the recipient with the encrypted message. The recipient decrypts the digital envelope using a private key and then uses the symmetric key to unlock the original message.

FIG. 2 graphically illustrates the relationships of the patient, healthcare provider, employer, insurer, electronic verification sources and verification specialists within an exemplary electronic patient registration verification and payment system formed in accordance with the present invention. The described exemplary electronic patient registration verification and payment system gives users considerable freedom to manage, maintain and utilize the functionality of the system. For example, patients 100 can, through a personal computer and the like, create new accounts 102 including an online registration and payment application for other members of their family which they may then complete. In another example, healthcare providers can create a new account for a patient including an online registration and payment application which the patient may then complete.

An exemplary system may send the notification by any of a number of conventional means, such as by email, fax, text or a combination thereof. In one embodiment, an exemplary system may assign a contact method based upon the patient's preference for receiving registration and payment information requests. Further, an exemplary system may automatically send an email or text to patients which includes instructions on how to access the patient registration verification and payment system electronically (e.g. online) as well as requests for the updating or clarifying of patient registration and payment information. An exemplary system may compare existing data to newly entered data and archive existing data to a history table. In another example, the system may automatically send an email or text when a withdrawal has been made from one or many of his or her financial accounts 104.

An exemplary embodiment of the present invention may also provide instant access to a patient's electronic registration and payment record by healthcare providers from any geographic location. In one embodiment, a healthcare provider may view the record of an existing patient's registration and payment information 106. In another embodiment, the healthcare provider may only view the record of an existing patient's registration and may not view the payment information. In addition, the described exemplary system may identify registration requirements for a particular healthcare provider including the parameters for custom patient medical history information 108. The described exemplary system may then automatically contact patients to request the custom medical history information 104.

For example, in the online verification and payment system of the present invention, an encrypted request for verification may be included as parameters on an HTTPS query string to reference data verification sites 120, such as insurers. An exemplary system may then auto-update the database with matched information or auto-generate electronic work prompts for ClipboardMD verification specialists to manually verify patient registration information for which no reference data verification source exists. A data specialist may then utilize a fax server or other similar means to verify the patient's registration and payment information 122.

In an exemplary embodiment of the present invention, the received verification information may be archived in an online data repository, allowing web access and tracking. For example, in the described exemplary embodiment, electronic information received from verification sites may be stored as data in a database. Similarly, verification information received from non-electronic sources may be scanned and stored as scanned images.

An exemplary system may also send the verified patient registration information to a web-server or storage database that furnishes data to the electronic information technology system used by the healthcare provider 124. In addition, the described exemplary system may receive from the same web-server or storage database data containing records of outstanding patient balances due the healthcare provider subsequent to the posting of all payments received from patients' insurers 126. Further, for an exemplary system, receipt of such data may then automatically initiate a procedure to match the received data of an outstanding balance due from a patient against the payment information stored for that patient.

In the online registration verification and payment system of the present invention, an encrypted instruction for electronic finds transfers may be included as parameters on an HTTPS request string to a financial automated clearinghouse 130. In one embodiment, the encrypted instruction may be automatically initiated immediately following the manual entry by the healthcare provider that electronically confirms the visit by a patient 110. In another embodiment, the encrypted instruction may be automatically initiated following a match of the outstanding patient balance data received from a healthcare provider's web-server or storage database against the payment information previously entered by patients. In an exemplary embodiment of the present invention, the encrypted instruction may include the withdrawal of funds from a financial account of a patient 132 whose finds transfer specifications have been entered into the ClipboardMD system by the patient and deposited into the ClipboardMD clearing bank account. Further, an exemplary system may automatically send an email to patients which includes information about the withdrawal of funds from their financial account 104.

The described exemplary electronic system of the present invention may also enable the patient to enter funds transfer specifications for more than one financial account 134 and to define the order from which funds may be withdrawn from each financial account as well as the minimum and maximum amounts of funds that may be withdrawn from each financial account. The described exemplary system may further comprise an accounting component that tracks all withdrawals of a patient's financial accounts and all deposits to a healthcare provider's financial account.

An exemplary embodiment of the present invention may permit a healthcare provider to enter instructions to have funds electronically transferred to his or her financial account to satisfy the payment responsibility of the patient. In one embodiment, the instruction may include the withdrawal of all funds due from the patient from the ClipboardMD clearing bank account and deposited into the financial account of the healthcare provider 136 whose funds transfer specifications have been entered into the ClipboardMD system by the healthcare provider. In another embodiment, the instruction may indicate that a series of future transfers, in lieu of a single transfer, is to be performed to satisfy the complete payment responsibility of the patient.

In one embodiment of the present invention, the patient registration information may be composed of elements that conform to a standardized programming language such as, for example, the extensible markup language (XML) specification. As is known in the art, XML is a markup language for documents containing structured information. Structured information contains both content (words, data, etc.) and some indication of what function that content performs. The utilization of a standardized programming language further promotes the automatic utilization of the patient registration information across enterprise-wide databases to capture or transfer registration and payment data.

The described exemplary system may also import patient registration and payment information from a variety of external data sources using, for example, the XML specification. For example, an XML data file from an employer 140 or health insurer 142 may be electronically captured and the data then imported into the registration verification and payment system ClipboardMD processing unit 70. In one embodiment of the present invention, employers who offer flexible spending accounts (FSA) to their employees may electronically transmit registration and payment data that would then be imported to auto-populate both registration and payment data tables.

FIG. 3 graphically illustrates the logic flow of an exemplary patient registration verification and payment process in accordance with the present invention. In one embodiment, patients 200 may logon to the described exemplary electronic registration verification and payment system 220 and enter and/or edit their own registration and payment information online.

In an exemplary process, a patient must review and accept a terms of use and an information release agreement 240 before being allowed to complete a registration and payment information record. In addition, an exemplary system may assign each patient record a globally unique identifier (GUID). The described exemplary system may capture a scanned signature or an electronic signature for each patient and may digitally convert the captured signature. In one embodiment, a scanned-in signature may be saved in JPEG or TIFF format.

An exemplary system may require the patient to complete all mandatory data fields before submitting a registration and payment record for verification 250. An exemplary embodiment of the present invention allows for the assigning of required data fields, for example, by the patient's age and sex. For example, in one embodiment patients may be required to complete a set of data fields pertinent to the field of practice of the healthcare provider they intend to visit. In accordance with an exemplary embodiment of the present invention, the required fields may be assigned when a patient's record is created.

The described exemplary system may automatically initiate the verification process for patient registration and payment records immediately after the information is entered 260 or delay the verification process until the end of a specified time period when all records are batched together into a single, large file. The described exemplary system may retrieve electronic data from reference databases, financial clearinghouses, and insurance verification systems 270.

An exemplary system of the present invention may correlate the verification information received from external sources with the registration and payment information entered by the patient 280. The described exemplary system may auto-update the database for matched data. In addition, in one embodiment of the present invention, the described exemplary system may attempt to identify reasons for a mismatch between the verification data received from external sources and the registration and payment information entered by the patient.

In one embodiment of the present invention, the system may automatically track the receipt of verification information and may automatically re-send verification requests if information is not received 282. An exemplary embodiment of the present invention may also create and maintain a continuous calendar of re-verification of a patient's registration and payment information. For example, an exemplary system of the present invention may create a re-verification schedule in accordance with the requirements for re-verification of insurance coverage. Further, if such reference sources are either non-responsive or not available, unverified information may be routed to an electronic work distribution and reminder program to initiate manual verification of data by ClipboardMD verification specialists 290.

In an exemplary embodiment of the present invention, the system records the user identification and date and time for each piece of data entered and any and all subsequent changes to provide a complete audit trail for patient registration and payment information entered into the system. In this manner, the system transforms a patient's information from a static record into a dynamic, real-time comprehensive record that may be linked to enterprise-wide databases to capture or supplement other patient data 300.

In addition, in an exemplary embodiment of the present invention, the healthcare provider 310, which collects submitted verified registration and payment information, may also remotely logon to the system via a global computer network, such as, for example, the Internet, using a personal computer or the like 320. The described exemplary system may require the healthcare provider to agree to terms of use and information privacy guidelines before being allowed to view a patient's registration and, in another version of the present invention, the payment information record, as well 330. In addition, an exemplary system may capture an electronic signature of the healthcare provider. This signature may be captured either through electronic creation by the healthcare provider or by the scanning of a healthcare provider's actual signature.

In another embodiment of the present invention, the healthcare provider may query the processing unit 70 of the patient registration verification and payment system to view the verified record of a specified patient 340. An exemplary system of the present invention may enable the healthcare provider to print a physical copy of the verified patient record or download a digital copy generated, for example, in PDF format to the computer being utilized to access the system via the Internet.

In addition, in an exemplary embodiment, the healthcare provider may enter information into the system to confirm the visit and treatment of the patient 350. The described exemplary system may then automatically initiate the payment transfer process by transmitting an encrypted instruction for electronic funds transfers as parameters on an HTTPS query string to a financial automated clearinghouse or credit card transaction gateway 360. In one embodiment of the present invention, the instruction may include the withdrawal of funds from a financial account of the patient whose funds transfer specifications have been entered into the ClipboardMD system by the patient and the corresponding deposit into the ClipboardMD clearing bank account 370.

In another embodiment of the present invention, the automatically generated electronic instruction may include the withdrawal of funds from the ClipboardMD clearing bank account and the corresponding deposit into the financial account of the healthcare provider whose funds transfer specifications have been entered into the ClipboardMD system by the healthcare provider 380.

FIG. 4 graphically illustrates an exemplary process in accordance with the present invention involving an encounter between patient 400 and healthcare provider 410 when the patient presents for a medical encounter. The described exemplary ClipboardMD electronic system enables the healthcare provider to capture verified patient registration information and receive patient payment with a single ClipboardMD identification number. In an exemplary embodiment of the present invention, the patient may present his ClipboardMD card that contains a single, multi-digit alphanumeric identification number 420. The healthcare provider may then log into the website of the online registration and payment system and enter such identification number on a web page displayed once the log in process is completed 430.

In one embodiment of the present invention, the online registration and payment system aggregates verified registration data stored on system web servers that correlate to the patient linked to the alphanumeric identification number and, for example, generates a digital report saved in PDF format to facilitate the data entry of the report's contents into the information technology system used by the healthcare provider 440. Alternatively, an exemplary system may electronically transfer, in real time or in batch, the verified registration data directly to the web server of associated with the online information technology system used by the healthcare provider 450.

An exemplary online registration and payment system of the present invention may, upon the online entry 460 by or electronic import of data 470 from the healthcare provider confirming the visit by the patient, further initiate a series of electronic instructions to a financial automated clearinghouse to transfer funds from one or more of the previously specified financial accounts of the patient 480 to a previously specified financial account of the healthcare provider 490. An exemplary system may automatically send an email to patients that includes information about the withdrawal of funds from their financial account 485.

FIG. 5 graphically illustrates an online payment transfer process in accordance with an exemplary embodiment of the present invention. For online data entry of payment information, the described exemplary system enables the patient 500 to login for online access to their registration and payment information account using a personal computer or the like 510. The exemplary online registration and payment information account includes a set of pre-defined sections that may further comprise common informational questions for the patient to answer. In one embodiment of the present invention, patients may select the online section labeled medical payment account (MPA) 520 to enter, for example, account specifications 530 such as routing and transit number, account number and account title associated with a checking account 540. In another embodiment of the present invention, patients may enter, for example, account specifications such as account number, expiration date and security code associated with a credit or debit card 540.

The described exemplary system of the present invention may also import patient registration and payment information from employers 545 who offer flexible spending accounts (FSA) to their employees. In one embodiment of the present invention, registration and payment information is imported directly from, for example, XML data files prepared by the employer. Importing registration and payment information may populate a range of data fields thereby mitigating the data entry effort required of the patient to complete his or her registration and payment account. An exemplary system of the present invention may then automatically send an email or text to patients which includes instructions on how to access the patient registration verification and payment system electronically. Additionally, in an exemplary embodiment, the system may require the patient to enter missing or incomplete information by continually contacting the patient via email or text until all information is complete.

Within the MPA online section for patients, the described exemplary system of the present invention enables patients to enter limits for each financial account created as to the minimum and maximum amounts that may be electronically withdrawn from such financial account at any one time 550. Additionally, the described exemplary system of the present invention enables patients to designate an order of priority for withdrawals made from each financial account created. For example, a patient may designate his or her checking account as the first financial account to be accessed for electronic withdrawals.

The described exemplary system of the present invention may auto-update the medical payment account database 560 and then automatically transmit an encrypted instruction for financial account verification as parameters on an HTTPS request string to a financial automated clearinghouse or credit card transaction gateway 570. In one embodiment, if the electronic data received from the financial automated clearinghouse indicates the financial account designated by the patient as the first priority for electronic withdrawals has insufficient funds for a particular withdrawal, the described exemplary system of the present invention then initiates a new HTTPS request string containing parameters of the second priority financial account as designated by the patient 580. In an exemplary embodiment of the present invention, funds are then withdrawn from the patient financial account and deposited in full into the ClipboardMD clearing bank account 590. The described exemplary system may further comprise an accounting component that tracks all withdrawals from a patient's financial accounts.

For online data entry of deposit information, the described exemplary system of the present invention enables the healthcare provider 600 to login for online access to their electronic registration and payment processing account using a personal computer or the like 610. The exemplary online registration and payment processing account may comprise a set of pre-defined sections that enable the healthcare provider to initiate a series of dynamic procedures. In one embodiment, healthcare providers may select the online section labeled medical payment account (MPA) 620 to enter, for example, account specifications 630 such as routing and transit number, account number and account title associated with the checking account 640 they may designate to receive electronic transfers of patient payments.

In an exemplary embodiment, the system of the present invention records the online entry by the healthcare provider to confirm a visit by the patient and then automatically transmits an encrypted instruction 650 for a transfer of funds from the ClipboardMD clearing bank account and corresponding deposit into the financial account designated by the healthcare provider 660 as parameters on an HTTPS request string to a financial automated clearinghouse. The described exemplary system of the present invention may further comprise an accounting component that tracks all deposits into a healthcare provider's financial account.

Some of the key features and advantages of the electronic patient registration verification and payment system of the present invention include, but are not limited to, the following:

1) Patients enter registration information online once for any healthcare provider;

2) The system archives any updated information to create an audit trail;

3) Patients provide an electronic signature and scanned copy of signature for files;

4) Registration information is verified for accuracy, completeness, and validity prior to transferring this information to the healthcare provider;

5) Patients can enter payment instructions regarding minimums and maximums to withdraw from any account as well as more than one account; the system checks for available funds in a first priority account and then a second account, a third account, etc., until sufficient funds are collected;

6) Registration and payment information can be acquired from employers offering Flex Spending Accounts and insurers;

7) A single ID (identification) number is all that is needed to transfer verified registration information and patient payment to the healthcare provider; and 8) Payments are automatically transferred to the healthcare provider either at the time of service or after all insurance payments are posted thereby leaving an outstanding patient balance.

Some of the key features and advantages of the electronic patient registration verification and payment method of the present invention include, but are not limited to, the following:

1) Electronic interfaces replace most of the manual activity currently used by healthcare providers to conduct the verification process;

2) Where electronic sources are not available, information is forwarded to verification specialists with time-sensitive prompts;

3) Patients are notified by email or text sent to specified addresses, such as email, cell phone, etc., when information is missing or needs to be updated;

4) Patients are notified in the same manner as mentioned above when withdrawals are made from their accounts;

5) Healthcare providers are able to customize registration data points; patients are notified of specific data requirements so they can enter the information prior to their medical encounter; and 6) Registration information can be sent to the healthcare provider by secure facsimile transmission, or is displayed online following secure login, or is electronically transferred to their online information technology system.

Thus, in accordance with a preferred form of the present invention, a method for electronically verifying patient registration information and transferring payments from patients to healthcare providers includes the steps of collecting registration and payment information from patients in a common format through an interface to a global network, collecting registration and payment information from employers and insurers in a plurality of formats, storing collected registration and payment information in a dynamic database, verifying collected registration information with external sources through secure electronic interfaces, transferring verified patient registration information to healthcare providers in a plurality of formats, collecting visit confirmation and patient balances information via a plurality of formats, and effecting transfers of funds from one or more patient financial accounts to financial accounts of healthcare providers through secure electronic interfaces.

Preferably, the step of collecting registration and payment information from patients includes the step of collecting information over the Internet or stored on storage media.

Furthermore, even more preferably, the method includes the step of authenticating patient registration and payment information with an electronic or scanned signature. Preferably, the step of authenticating the patient registration and payment information with an electronic signature or scanned signature includes the steps of assigning a Global Unique Identification (GUID) upon login and capturing a scanned signature from a paper document.

In another preferred form of the invention, the method further includes the step of assigning a random, single, alphanumeric identification number to the patient used to initiate the transfer of verified patient registration information and payment to the healthcare provider.

In yet another preferred form of the invention, the method includes the step of collecting patient payment information, and, even more preferably, the step of collecting patient payment information includes the steps of enabling the patient to enter the identification specifications of one or more financial accounts to fund electronic withdrawals, enabling the patient to assign to each financial account an order of priority for withdrawals to be electronically effected, and enabling the patient to designate minimum and maximum limits for electronic withdrawals of each financial account.

In a further preferred form of the present invention, the method further includes the step of verifying collected patient registration and payment information with external sources. The step of verifying collected patient registration and payment information preferably includes the steps of comparing registration information submitted by the patient with verified registration information from external sources to provide at least one of matched information, incorrect information and invalid information. If matched information is provided, then the method includes the step of auto-updating the database with the matched information. If incorrect information is provided, then the method includes the step of auto-marking the incorrect information. If invalid information is provided, then the method includes the step of auto-marking the invalid information. The step of verifying collected patient registration and payment information may further include the steps of receiving verification information from non-electronic sources and storing the verification information as scanned images, and manually updating the database through the use of electronic work distribution and reminder prompts.

Furthermore, the method described above may further include the step of creating and maintaining a re-verification calendar of said patient registration and payment information.

In another form of the present invention, the step of storing collected patient registration and payment information in a dynamic database may include the steps of comparing existing registration and payment information to verified registration and payment information and archiving existing registration and payment information to a history table.

In yet another form of the present invention, the step of transferring verified patient registration information to healthcare providers in a plurality of formats may include at least one of the steps of generating a report of verified patient registration information for online viewing, generating a report of verified patient registration information in PDF format for printing, emailing or faxing and generating an electronic data file of verified patient registration information for electronic transfer to web servers supporting online information technology systems used by healthcare providers.

In accordance with another form of the present invention, the step of collecting visit confirmation and patient balances information from healthcare providers via a plurality of formats may include at least one of the steps of collecting information over the Internet following login by the healthcare provider and collecting information through the import of data from real-time and batch electronic transfers.

In accordance with yet another form of the present invention, the step of effecting transfers of funds from one or more patient financial accounts to financial accounts of healthcare providers through secure electronic interfaces may include at least one of the steps of auto-generating electronic instructions to a financial automatic clearinghouse to debit one or more financial accounts of a patient and to credit a predetermined clearing account for same amount, auto-generating electronic instructions to a financial automatic clearinghouse to debit a predetermined clearing account and to credit the financial account of a healthcare provider for the same amount and auto-generating accounting records of the transfers of funds from patient financial accounts and funds transferred to healthcare provider financial accounts.

The method of the present invention may further include the step of generating user-defined reports on patient registration and payment information.

An electronic patient registration verification and payment system, formed in accordance with the present invention, preferably includes means for collecting registration and payment information from patients in a common format through an interface to a global network, means for collecting registration and payment information from employers and insurers in a plurality of formats, means for storing collected registration and payment information in a dynamic database, means for transferring verified patient registration information to healthcare providers in a plurality of formats, means for collecting visit confirmation and patient balances information via a plurality of formats and means for effecting transfers of funds from one or more patient financial accounts to financial accounts of healthcare providers through secure electronic interfaces.

Even more preferably, the electronic patient registration verification and payment system further includes means for generating verified registration information including copies of records from external sources. Even more specifically, the electronic patient registration verification and payment system further includes means for creating and maintaining a calendar of re-verification of a patient's registration and payment information.

Even more specifically, the means for collecting registration and payment information from patients includes means for collecting information over the Internet or stored on storage media.

The electronic patient registration verification and payment system, in an even more preferred form, further includes means for authenticating patient registration and payment information with an electronic or scanned signature. The means for authenticating the patient registration and payment information with an electronic signature or scanned signature preferably includes means for assigning a Global Unique Identification (GUID) upon login and means for capturing a scanned signature from a paper document.

In yet another preferred form of the present invention, the electronic patient registration verification and payment system further includes means for assigning a random, single, alphanumeric identification number to the patient used to initiate the transfer of verified patient registration information and payment to the healthcare provider. Even more preferably, the system further includes means for collecting patient payment information. Such means for collecting patient payment information may include means for enabling the patient to enter the identification specifications of one or more financial accounts to fund electronic withdrawals, means for enabling the patient to assign to each financial account an order of priority for withdrawals to be electronically effected and means for enabling the patient to designate minimum and maximum limits for electronic withdrawals of each financial account.

The electronic patient registration verification and payment system, in another preferred form, includes means for verifying collected patient registration and payment information with external sources. The means for verifying collected patient registration and payment information may include means for comparing registration information submitted by the patient with verified registration information from external sources to provide at least one of matched information, incorrect information and invalid information. If matched information is provided, then the means for verifying collected patient registration and payment information of the system further includes means for auto-updating the database with the matched information. If incorrect information is provided, then the means for verifying collected patient registration and payment information of the system further includes means for auto-marking the incorrect information. If invalid information is provided, then the means for verifying collected patient registration and payment information of the system further includes means for auto-marking the invalid information. The system may preferably include means for receiving verification information from non-electronic sources and storing the verification information as scanned images and means for updating the database through the use of electronic work distribution and reminder prompts. Also, the system may further include means for creating and maintaining a re-verification calendar of said patient registration and payment information.

In yet another preferred form of the invention, the means for storing collected patient registration and payment information in a dynamic database of the electronic patient registration verification and payment system includes means for comparing existing registration and payment information to verified registration and payment information and means for archiving existing registration and payment information to a history table.

Even more preferably, the means for transferring verified patient registration information to healthcare providers in a plurality of formats of the system includes at least one of means for generating a report of verified patient registration information for online viewing, means for generating a report of verified patient registration information in PDF format for printing, emailing or faxing and means for generating an electronic data file of verified patient registration information for electronic transfer to web servers supporting online information technology systems used by healthcare providers.

The means for collecting visit confirmation and patient balances information from healthcare providers via a plurality of formats of a preferred form of the system includes at least one of means for collecting information over the Internet following login by the healthcare provider and means for collecting information through the import of data from real-time and batch electronic transfers.

In the electronic patient registration verification and payment system, the means for effecting transfers of funds from one or more patient financial accounts to financial accounts of healthcare providers through secure electronic interfaces may include at least one of means for auto-generating electronic instructions to a financial automatic clearinghouse to debit one or more financial accounts of a patient and to credit a predetermined clearing account for same amount, means for auto-generating electronic instructions to a financial automatic clearinghouse to debit a predetermined clearing account and to credit the financial account of a healthcare provider for the same amount and means for auto-generating accounting records of the transfers of funds from patient financial accounts and funds transferred to healthcare provider financial accounts. Furthermore, the electronic patient registration verification and payment system may further include means for generating user-defined reports on patient registration and payment information.

With respect to all of the "means" stated above, a microprocessor in the system, or software, may be used to perform the various noted functions.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A computer-implemented method for use between a patient and healthcare provider independently of any health plan administrative system prior to the rendering of medical services by the healthcare provider to the patient for electronically verifying the patient's registration information and transferring payments from the patient to the healthcare provider, comprising the steps of:

collecting registration and method of payment information directly from patients in a common format through a graphical user interface, designed specifically for use by patients, prior to the rendering of medical services by the healthcare provider to the patient, as part of a secure patient registration verification and payment processing computer system, stored on secure dynamic database servers that are independent of any health plan administrative system, connected to a global network;

collecting patient registration and method of payment information from employers and insurers contained in a plurality of digital storage formats, via secure electronic data transfers prior to the rendering of medical services by the healthcare provider to the patient as part of the secure patient registration verification and payment processing computer system, stored on secure dynamic database servers that are independent of any health plan administrative system;

securely storing said collected patient registration and method of payment information received from patients, employers and/or insurers in a secure dynamic database prior to the rendering of medical services by the healthcare provider to the patient as part of the secure patient registration verification and payment processing computer system, stored on secure dynamic database servers that are independent of any health plan administrative system;

verifying collected patient registration and method of payment information by transmitting data inquiry files derived from this secure dynamic database, stored on secure dynamic database servers that are independent of any health plan administrative system, to another computer system containing data stored by external sources through secure electronic interfaces, receiving related data response files from this computer containing data stored by external sources through secure electronic interfaces, and electronically comparing collected patient registration and method of payment information received from patients, employers and/or insurers to the patient registration and method of payment information received from external sources prior to the rendering of medical services by the healthcare provider to the patient;

transferring, from the secure patient registration verification and payment processing computer system, stored on secure dynamic database servers that are independent of any health plan administrative system, verified patient registration information to healthcare providers in a common format by electronic fax or through a graphical user interface, designed specifically for use by healthcare providers, prior to the rendering of medical services by the healthcare provider to the patient, as part of the secure patient registration verification and payment processing computer system, stored on secure dynamic database servers that are independent of any health plan administrative system, connected to a global network;

collecting a confirmation of the patient's appearance from the healthcare provider in addition to amount owed by the patient to the healthcare provider via a plurality of formats and stored on secure dynamic database servers that are independent of any health plan administrative system; and electronically executing the transfer of funds using one or more said methods of payment derived from the method of payment information previously provided by the patient to a financial account previously provided by the healthcare provider through secure electronic interfaces stored on secure dynamic database servers that are independent of any health plan administrative system.

2. The method of claim 1, wherein the step of collecting registration and method of payment information directly from patients comprises the step of collecting, prior to the rendering of medical services by the healthcare provider to the patient, registration and method of payment information through said graphical user interface, designed specifically for use by patients, as part of the secure patient registration verification and payment processing computer system, stored on the secure dynamic database servers that are independent of any health plan administrative system, connected to a global network.

3. The method of claim 1, wherein the step of collecting, prior to the rendering of medical services by the healthcare provider to the patient, patient registration and payment information from employers and insurers comprises the step of collecting information stored in a plurality of digital storage formats via secure electronic data transfers as part of the secure patient registration verification and payment processing computer system, stored on the secure dynamic database servers that are independent of any health plan administrative system.

4. The method of claim 1, further comprising the step of authenticating patient registration and method of payment information with an electronic or scanned signature stored on the secure dynamic database servers that are independent of any health plan administrative system.

5. The method of claim 4, wherein the step of authenticating the patient registration and payment information with an electronic signature or scanned signature comprises the steps of:

assigning a random, single, alphanumeric identification number or Global Unique Identification (GUID) upon login by the patient to said graphical user interface, designed specifically for use by patients, as part of the secure patient registration verification and payment processing computer system, stored on the secure dynamic database servers that are independent of any health plan administrative system, connected to a global network; and capturing an electronic acknowledgement by patient via said graphical user interface, designed specifically for use by patients, as part of the secure patient registration verification and payment processing computer system, stored on the secure dynamic database servers that are independent of any health plan administrative system, connected to a global network; or capturing a scanned signature from a paper document.

6. The method of claim 1, further comprising the step of assigning a random, single, alphanumeric identification number or Global Unique Identification (GUID) to the patient used to initiate the transfer of verified patient registration information and payment stored on the secure dynamic database servers that are independent of any health plan administrative system to the healthcare provider.

7. The method of claim 1, further comprising the step of collecting patient method of payment information, the step of collecting patient method of payment information comprising the steps of:

enabling the patient to enter, in real time, in a common format, via said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network, the account specifications, that include bank name or type of credit card and account number, of one or more financial accounts to fund electronic debits;

enabling the patient to assign, in real time, in a common format, via said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network, to each financial account an order of priority for debits to be electronically effected; and enabling the patient to designate, in real time, in a common format, via said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network, minimum and maximum amounts to be electronically debited from each financial account.

8. The method of claim 1, further comprising the step of electronically verifying collected patient registration and method of payment information with external sources, the step of verifying collected patient registration and method of payment information comprising the steps of:

electronically comparing, in real time, registration information submitted by the patient via said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network, with registration information received from external sources to provide at least one of matched information, incorrect information or invalid information;

if all registration information provided by the patient matches that received from external sources, then auto-marking the patient record in the secure dynamic database servers that are independent of any health plan administrative system as 'matching';

if selected registration information provided by the patient does not match that received from external sources, while other registration information does match, then auto-marking only the selected information of the patient record in the secure dynamic database servers that are independent of any health plan administrative system as 'incorrect';

if all information provided by the patient does not match that received from external sources, then auto-marking the patient record in the secure dynamic database servers that are independent of any health plan administrative system as 'invalid';

receiving patient registration verification information from non-electronic sources and storing patient registration verification information as scanned images in database servers that are independent of any health plan administrative system, connected to a global network; and manually updating the patient record in the secure dynamic database through the use of electronic work distribution and reminder prompts transmitted to administrative personnel via said graphical user interface, designed specifically for use by administrative personnel, as part of the secure patient registration verification and payment processing computer system, stored on the secure dynamic database servers that are independent of any health plan administrative system, connected to a global network.

9. The method of claim 8, further comprising the step of creating and maintaining a re-verification calendar of said patient registration and method of payment information.

10. The method of claim 1, wherein the step of securely storing collected patient registration and method of payment information in the secure dynamic database as part of the secure patient registration verification and payment processing computer system, stored on database servers that are independent of any health plan administrative system, comprises the steps of:

electronically comparing existing patient registration and method of payment information to verified patient registration and method of payment information, stored on the secure dynamic database servers that are independent of any health plan administrative system; and archiving existing patient registration and method of payment information to a history table in the secure dynamic database as part of the secure patient registration verification and payment processing computer system, stored on database servers that are independent of any health plan administrative system.

11. The method of claim 1, wherein the step of transferring verified patient registration information to healthcare providers in a common format by electronic fax or through said graphical user interface, designed specifically for use by healthcare providers prior to the rendering of medical services by the healthcare provider to the patient, as part of the secure patient registration verification and payment processing computer system, stored on the secure dynamic database servers that are independent of any health plan administrative system, connected to a global network comprises at least one of the steps of:

generating a report of verified patient registration information in a common format viewed by healthcare providers through said graphical user interface, designed specifically for use by healthcare providers as part of the secure patient registration verification and payment processing computer system, stored on the secure dynamic database servers that are independent of any health plan administrative system, connected to a global network;

generating a report of verified patient registration information in a common PDF format transferred by electronic fax to healthcare providers;

generating an electronic data file of verified patient registration information for secure electronic transfer from the secure dynamic database to web servers supporting computer systems connected to a global network and used by healthcare; and generating an electronic data file of verified patient registration information for secure electronic transfer from the secure dynamic database to a database server contained in a computer system used by healthcare providers.

12. The method of claim 1, wherein the step of collecting confirmation of the patient's appearance from the healthcare provider in addition to any amount owed by the patient to the healthcare provider via a plurality of formats comprises at least one of the steps of:

collecting a confirmation, in a common format, over the Internet following login by the healthcare provider to said graphical user interface, designed specifically for use by healthcare providers, as part of the secure patient registration verification and payment processing computer system, stored on the secure dynamic database servers that are independent of any health plan administrative system, connected to a global network;

collecting a confirmation by the healthcare provider via an electronic fax system that captures and stores the fax image, in real time, in the secure dynamic database, as part of the secure patient registration verification and payment processing computer system, stored on database servers that are independent of any health plan administrative system; and collecting a confirmation through the secure real-time and batch electronic transfer of data from a database server contained in a computer system used by healthcare providers and storing in the secure dynamic database servers that are independent of any health plan administrative system.

13. The method of claim 1, wherein the step of electronically executing the transfer of funds using one or more methods of payment derived from the methods of payment information previously provided by the patient to a financial account previously provided by the healthcare provider through secure electronic interfaces comprises at least one of the steps of:
- auto-generating secure electronic instructions from database servers that are independent of any health plan administrative system to a financial automatic clearinghouse to debit one or more financial accounts of the patient and to credit a predetermined clearing account for the same amount;
- auto-generating secure electronic instructions from database servers that are independent of any health plan administrative system to a financial automatic clearinghouse to debit the predetermined clearing account and to credit the financial account of the healthcare provider for the same amount; and
- auto-generating accounting records of the transfers of funds from the patient financial accounts stored on the secure dynamic database servers that are independent of any health plan administrative system and the transfer of funds transferred to the healthcare provider financial account.

14. The method of claim 1, further comprising the step of enabling healthcare providers to generate, via said graphical user interface, designed specifically for use by healthcare providers, as part of the secure patient registration verification and payment processing computer system, stored on the secure dynamic database servers that are independent of any health plan administrative system, connected to a global network, user-defined reports on patient registration and payment information in real time.

15. A secure electronic patient registration verification and payment system for use between a patient and healthcare provider independently of any health plan administrative system prior to the rendering of medical services by the healthcare provider to the patient and for electronically verifying the patient's registration information and transferring payments from the patient to the healthcare provider, comprising:
- a graphical user interface, designed specifically for use by patients prior to the rendering of medical services by the healthcare provider to the patient, for collecting registration and method of payment information directly from patients in a common format, forming part of the secure patient registration verification and payment processing computer system, stored on the secure dynamic database servers that are independent of any health plan administrative system, connected to a global network;
- secure electronic data transfer logic for collecting patient registration and method of payment information from employers and insurers prior to the rendering of medical services by the healthcare provider to the patient contained in a plurality of digital storage format, forming part of the secure patient registration verification and payment processing computer system, stored on the secure dynamic database servers that are independent of any health plan administrative system;
- a secure, dynamic database for storing collected patient registration and method of payment information received from patients, employers and/or insurers prior to the rendering of medical services by the healthcare provider to the patient forming part of the secure patient registration verification and payment processing computer system, that is independent of any health plan administrative system;
- patient registration verification computer logic for verifying collected patient registration and method of payment information with external sources through secure electronic interfaces and generating verified patient and method of payment information;
- a graphical user interface, designed specifically for use by healthcare providers, for transferring verified patient registration information to healthcare providers prior to the rendering of medical services by the healthcare provider to the patient in a common format forming part of the secure patient registration verification and payment processing computer system, stored on the secure dynamic database servers that are independent of any health plan administrative system;
- a computer-implemented interface for collecting visit confirmation and patient balance information via an electronic system that captures and stores electronic information in said dynamic database, forming part of the secure patient registration verification and payment processing computer system, stored on the secure dynamic database servers that are independent of any health plan administrative system; and
- patient payment logic that is operable for electronically effecting transfers of funds from one or more financial accounts of a patient to a financial account of a healthcare provider through secure electronic interfaces, forming part of a secure patient registration verification and payment processing computer system, stored on the secure dynamic database servers that are independent of any health plan administrative system.

16. The secure electronic patient registration verification and payment system of claim 15, further comprising computer logic for auto-creating and maintaining a calendar of re-verification of patient registration and method of payment information.

17. The secure electronic patient registration verification and payment system of claim 15, further comprising patient registration verification logic that is operable in real time for collecting registration and payment information directly from patients via a graphical user interface, designed specifically for use by patients prior to the rendering of medical services by the healthcare provider to the patient, forming part of the secure patient registration verification and payment processing computer system, stored on the secure dynamic database servers that are independent of any health plan administrative system, connected to a global network.

18. The secure electronic patient registration verification and payment system of claim 15, further comprising secure data transfer logic that is operable in real time and batch mode for collecting patient registration and method of payment information from employers and insurers prior to the rendering of medical services by the healthcare provider to the patient stored on the secure dynamic database servers that are independent of any health plan administrative system.

19. The secure electronic patient registration verification and payment system of claim 15, further comprising data and image capture logic that is operable in real time for authenticating patient registration and method of payment information with an electronic or scanned signature.

20. The secure electronic patient registration verification and payment system of claim 19, wherein the data and image capture logic for authenticating the patient registration and method of payment information in real time with an electronic signature or scanned signature comprises:

computer logic that is operable in real time for automatically assigning a random, single, alphanumeric identification number or Global Unique Identification (GUID) upon login by the patient to said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network; and at least one of:

computer logic that is operable in real time for capturing an electronic acknowledgement by patient via said graphical user interface, designed specifically for use by patients prior to the rendering of medical services by the healthcare provider to the patient, as part of the secure patient registration verification and payment processing computer system, stored on the secure dynamic database servers that are independent of any health plan administrative system, connected to a global network; and a computer-implemented fax interface for capturing a scanned signature from a paper document via an electronic fax system that captures and stores fax images in said dynamic database, forming part of the secure patient registration verification and payment processing computer system, stored on the secure dynamic database servers that are independent of any health plan administrative system connected to a global network.

21. The secure electronic patient registration verification and payment system of claim 15, further comprising computer logic that is operable in real time for automatically assigning a random, single, alphanumeric identification number or Global Unique Identification (GUID) to a record of the patient stored in the dynamic database servers that are independent of any health plan administrative system, that is then used to execute the transfer of verified patient registration information and payment to the healthcare provider prior to the rendering of medical services by the healthcare provider to the patient.

22. The secure electronic patient registration verification and payment system of claim 15, wherein the graphical user interface, designed specifically for use by patients as part of the secure patient registration verification and payment processing computer system, stored on the secure dynamic database servers that are independent of any health plan administrative system, connected to a global network, enables the patient to enter the account specifications that include bank name or type of credit card and account number of one or more financial accounts to fund electronic debits, enables the patient to assign, in real time, to each financial account an order of priority for debits to be electronically effected, and enables the patient to designate, in real time, minimum and maximum amounts to be electronically debited from each financial account.

23. The secure electronic patient registration verification and payment system of claim 15, wherein the patient registration verification computer logic is operable in real time for verifying collected patient registration and method of payment information with external sources, and wherein the patient registration verification computer logic further comprises:

patient registration comparison logic that is operable in real time for comparing registration information submitted by the patient prior to the rendering of medical services by the healthcare provider to the patient, stored on the secure dynamic database servers that are independent of any health plan administrative system, with registration information from external sources to provide at least one of matched information, incorrect information or invalid information;

wherein if matched information is provided, said patient registration comparison logic that is operable in real time auto-marks a record of the patient in the secure dynamic database servers that are independent of any health plan administrative system as 'matching';

wherein if incorrect information is provided, said patient registration comparison logic that is operable in real time auto-marks a record of the patient in the secure dynamic database servers that are independent of any health plan administrative system as 'incorrect'; and wherein if invalid information is provided, said patient registration comparison logic that is operable in real time auto-marks a record of the patient in the secure dynamic database servers that are independent of any health plan administrative system as 'invalid';

said patient registration comparison logic receiving verification information from non-electronic sources and storing the verification information in the secure dynamic database servers that are independent of any health plan administrative system as scanned images; and said patient registration comparison logic updating the record of the patient in the secure dynamic database servers that are independent of any health plan administrative system through the use of electronic work distribution and reminder prompts.

24. The secure electronic patient registration verification and payment system of claim 23, wherein said patient registration verification computer logic creates and maintains a re-verification calendar of said patient registration and method of payment information.

25. The secure electronic patient registration verification and payment system of claim 15, wherein said patient registration verification computer logic compares existing registration and method of payment information stored on the secure dynamic database servers that are independent of any health plan administrative system to verified registration and payment information, and archives existing registration and method of payment information to a history table in the secure dynamic database servers that are independent of any health plan administrative system.

26. The secure electronic patient registration verification and payment system of claim 15, wherein the patient registration verification computer logic generates prior to the rendering of medical services by the healthcare provider to the patient verified patient registration information for healthcare providers in a common format designed specifically for use by healthcare providers, as part of the secure patient registration verification and payment processing computer system, stored on the secure dynamic database servers that are independent of any health plan administrative system, connected to a global network and provides at least one of the following:

a report of verified patient registration information in a common format viewed by healthcare providers through said graphical user interface, designed specifically for use by healthcare providers, as part of the secure patient registration verification and payment processing computer system, stored on the secure dynamic database servers that are independent of any health plan administrative system, connected to a global network;
a report of verified patient registration information in a common PDF format transferred by fax to healthcare providers;
an electronic data file of verified patient registration information for secure electronic transfer to web servers supporting computer systems used by healthcare providers; and
an electronic data file of verified patient registration information, stored on the secure dynamic database servers that are independent of any health plan administrative system, for secure electronic transfer to a database server contained in a computer system used by healthcare providers.

27. The secure electronic patient registration verification and payment system of claim 15, wherein said patient registration verification computer logic collects a confirmation of the patient's appearance from the healthcare provider in addition to any amount owed by the patient to the healthcare provider, wherein the confirmation is collected in at least one of the following methods:
collecting the confirmation, in a common format, over the Internet following login by the healthcare provider to said graphical user interface, designed specifically for use by healthcare providers, as part of the secure patient registration verification and payment processing computer system, stored on the secure dynamic database servers that are independent of any health plan administrative system, connected to a global network;
collecting the confirmation by the healthcare provider via an electronic fax system that captures and stores fax images in the secure dynamic database servers that are independent of any health plan administrative system, forming part of the secure patient registration verification and payment processing computer system; and
collecting the confirmation through the secure real-time and batch electronic transfer of data from a database server contained in a computer system used by healthcare providers.

28. The secure electronic patient registration verification and payment system of claim 15, wherein the patient payment logic executes the transfer of funds from one or more methods of payment derived from the methods of payment information previously provided by the patient and stored in the secure dynamic database servers that are independent of any health plan administrative system to financial accounts previously provided by the healthcare provider through secure electronic interfaces by at least one of the following:
auto-generating secure electronic instructions to a financial automatic clearinghouse to debit one or more financial accounts of the patient stored on the secure dynamic database servers that are independent of any health plan administrative system and to credit a predetermined clearing account for the same amount;
auto-generating secure electronic instructions to a financial automatic clearinghouse to debit the predetermined clearing account and to credit the financial account of the healthcare provider for the same amount; and
auto-generating accounting records of the transfers of funds from the patient financial accounts stored on the secure dynamic database servers that are independent of any health plan administrative system and the transfer of funds transferred to the healthcare provider financial accounts.

29. The secure electronic patient registration verification and payment system of claim 15, wherein the patient registration verification computer logic generates user-defined reports on patient registration and payment information in real time via said graphical user interface, designed specifically for use by healthcare providers as part of the secure patient registration verification and payment processing computer system, stored on the secure dynamic database servers that are independent of any health plan administrative system, connected to a global network.

30. The secure electronic patient registration verification and payment system of claim 15, wherein said patient registration verification computer logic comprises a processor-based device.

31. The secure electronic patient registration verification and payment system of claim 15, wherein said patient registration verification computer logic comprises computer-executable software instructions stored to the secure dynamic database servers that are independent of any health plan administrative system and a processor for executing said software instructions.

* * * * *